United States Patent
Bruckmann et al.

(10) Patent No.: US 12,329,679 B2
(45) Date of Patent: Jun. 17, 2025

(54) APPARATUS WITH SENSOR FEEDBACK

(71) Applicant: Solventum Intellectual Properties Company, Maplewood, MN (US)

(72) Inventors: Thomas Bruckmann, Hilden (DE); Yvonne I. Lund, Roberts, WI (US); Michael W. T. Mansholt, Cologne (DE); Henning Reuter, Willich (DE); Jonathan V. Sry, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 975 days.

(21) Appl. No.: 17/250,716

(22) PCT Filed: Sep. 9, 2019

(86) PCT No.: PCT/IB2019/057583
§ 371 (c)(1),
(2) Date: Feb. 24, 2021

(87) PCT Pub. No.: WO2020/058802
PCT Pub. Date: Mar. 26, 2020

(65) Prior Publication Data
US 2021/0322206 A1 Oct. 21, 2021

Related U.S. Application Data

(60) Provisional application No. 62/733,682, filed on Sep. 20, 2018.

(51) Int. Cl.
*A61F 7/00* (2006.01)
*A61B 5/00* (2006.01)
*G16H 40/67* (2018.01)

(52) U.S. Cl.
CPC .......... *A61F 7/0097* (2013.01); *A61B 5/0008* (2013.01); *G16H 40/67* (2018.01);
(Continued)

(58) Field of Classification Search
CPC ............ A61F 7/0097; A61F 2007/0052; A61F 2007/0055; A61F 2007/0094; G16H 40/67; A61B 5/0008; A61B 2562/227
See application file for complete search history.

(56) References Cited

U.S. PATENT DOCUMENTS 5,817,003 A 10/1998 Moll
7,517,360 B2 * 4/2009 Frey ...................... A61F 7/0085
607/104
(Continued)

FOREIGN PATENT DOCUMENTS

WO WO 1999-044552 9/1999
WO WO 2009-049297 4/2009
(Continued)

OTHER PUBLICATIONS

Peter, "Automated closed-loop management of body temperature using forced-air blankets: preliminary feasibility study in a porcine model", BMC Anesthesiology, 2018, vol. 18, No. 80, 11 pgs.
(Continued)

*Primary Examiner* — Adam Z Minchella

(57) ABSTRACT

Aspects of the present disclosure relate to an apparatus for providing pressurized, thermally conditioned air, comprising a casing, a housing in the casing describing an airflow pathway with an air diffusing outlet proximate to an outlet opening for providing a stream of pressurized air through the outlet opening, a convective module disposed part of the housing and the outlet opening via the airflow pathway. The apparatus can include a first sensor input port adjacent to a portion of the casing and configured to receive a signal indicative of a first physiological indicator and a first sensor output port adjacent to a portion of the casing and configured to transmit the signal indicative of the first physiological indicator. The apparatus can include a controller configured
(Continued)

to determine a first physiological indicator value from the first sensor input port and perform at least one operation.

19 Claims, 9 Drawing Sheets

(52) U.S. Cl.
CPC . *A61B 2562/227* (2013.01); *A61F 2007/0052* (2013.01); *A61F 2007/0055* (2013.01); *A61F 2007/0094* (2013.01)

(56) References Cited

U.S. PATENT DOCUMENTS

| | | | |
|---|---|---|---|
| 8,231,664 B2 | 7/2012 | Kulstad | |
| 8,647,374 B2 | 2/2014 | Koewler | |
| 9,354,122 B2 | 5/2016 | Bieberich | |
| 2001/0056226 A1* | 12/2001 | Zodnik | G16H 40/67 |
| | | | 600/300 |
| 2002/0019586 A1* | 2/2002 | Teller | H04Q 3/00 |
| | | | 128/903 |
| 2003/0046762 A1* | 3/2003 | Stolpmann | A61G 7/05776 |
| | | | 5/710 |
| 2003/0182087 A1* | 9/2003 | Linley | G16H 40/67 |
| | | | 707/E17.116 |
| 2007/0177651 A1 | 8/2007 | Daugherty | |
| 2010/0023348 A1* | 1/2010 | Hardee | G06Q 50/00 |
| | | | 600/300 |
| 2010/0052914 A1 | 3/2010 | Tsai | |
| 2010/0130837 A1* | 5/2010 | Matott | A61B 5/07 |
| | | | 600/302 |
| 2011/0213274 A1* | 9/2011 | Telfort | A61B 7/003 |
| | | | 600/586 |
| 2012/0016258 A1* | 1/2012 | Webster | G01K 1/024 |
| | | | 600/549 |
| 2012/0197584 A1 | 8/2012 | Coates | |
| 2013/0278414 A1* | 10/2013 | Sprigg | A61B 5/746 |
| | | | 340/539.12 |
| 2017/0156923 A1* | 6/2017 | Utturkar | A61B 5/4836 |
| 2018/0140459 A1 | 5/2018 | Taylor | |
| 2018/0250159 A1* | 9/2018 | DeSeve, III | A61F 7/007 |

FOREIGN PATENT DOCUMENTS

| | | |
|---|---|---|
| WO | WO 2014-150572 | 9/2014 |
| WO | WO 2015-092627 | 6/2015 |
| WO | WO 2017-059333 | 4/2017 |
| WO | WO 2018-235019 | 12/2018 |

OTHER PUBLICATIONS

International Search Report for PCT International Application No. PCT/IB2019/057583, mailed on Dec. 9, 2019, 5 pages.

* cited by examiner

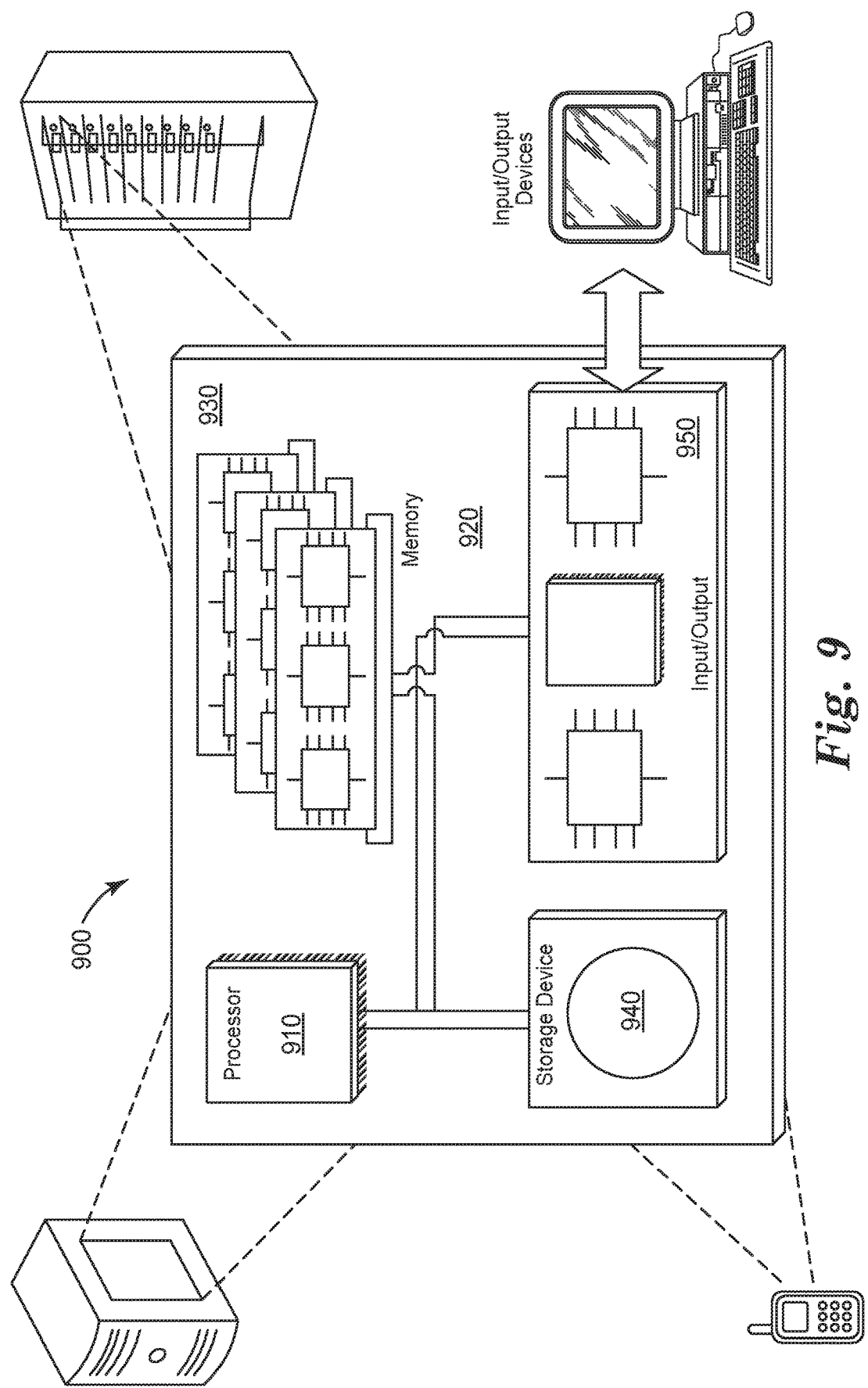

APPARATUS WITH SENSOR FEEDBACK

CROSS REFERENCE TO RELATED APPLICATIONS

This application is a national stage filing under 35 U.S.C. 371 of PCT/IB2019/057583, filed Sep. 9, 2019, which claims the benefit of Provisional Application No. 62/733,682, filed Sep. 20, 2018, the disclosures of which are incorporated by reference in their entirety herein.

BACKGROUND

Active warming systems can augment metabolic heating in the task of keeping the microenvironment near the skin warm. If the air in the microenvironment is warmer than the skin surface, some heat will enter the body. But even if the microenvironment is cooler than the skin, it can assist in preventing further heat loss. Such devices maintain a microenvironment that is warmer than is possible with passive systems.

Active warming systems can use conduction, infrared, or convection. One family of devices relies on heated air convection. Here, warm air is circulated through the air pocket, warming the skin surface and the insulating blanket. There may still be convective and conductive heat loss from the system, but the additional heat reduces or eliminates the need for the body to maintain the warmth of its microenvironment.

SUMMARY

Although active warming systems exist, existing convective active warming systems are not able to receive inputs directly from sensors and forward data from the sensor to a patient monitor. While some warming systems can indirectly receive temperature inputs from the sensors (e.g., through a medical monitor), this approach may result in excessive cables and introduce lag time.

Aspects of the present disclosure relate to an apparatus for providing pressurized, thermally conditioned air, comprising a casing, a housing in the casing describing an airflow pathway with an air diffusing outlet proximate to an outlet opening for providing a stream of pressurized air through the outlet opening, a convective module disposed part of the housing and the outlet opening via the airflow pathway. The apparatus can include a first sensor input port adjacent to a portion of the casing and configured to receive a signal indicative of a first physiological indicator and a first sensor output port adjacent to a portion of the casing and configured to transmit the signal indicative of the first physiological indicator. The apparatus can include a controller configured to determine a first physiological indicator value from the first sensor input port and perform at least one operation.

BRIEF DESCRIPTION OF DRAWINGS

FIG. 9 is a block diagram of a computing device, according to aspects of the present disclosure.

DETAILED DESCRIPTION

Aspects of the present disclosure relate to an apparatus configured to receive an input from a sensor and output the input from the sensor to a medical monitor. The apparatus can modify one or more settings of a convective module in response to the input. Additional aspects can relate to a system including a remote computer that accesses the physiological indicator data from the sensor from the apparatus or a logging unit to generate trends.

Figure 1:
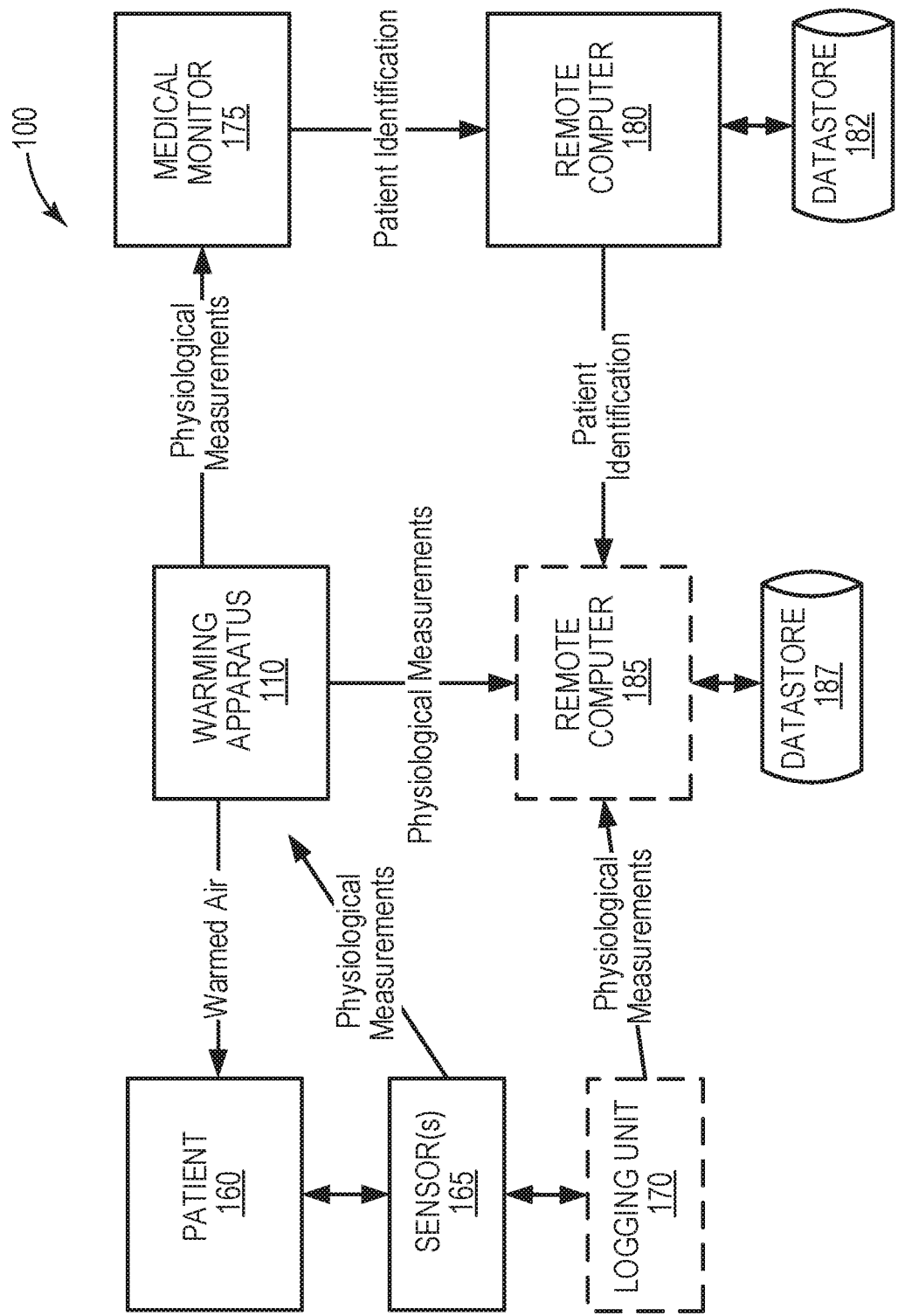
FIG. 1 is a block diagram of a system including an apparatus, according to aspects of the present disclosure.

FIG. 1 illustrates a system 100 for receiving data. System 100 can include an apparatus 110 that warms a patient 160 using generated heat. In at least one embodiment, the apparatus 110 uses convective, conductive, or radiative warming. Examples of convective warming can include apparatus commercially available under the trade designation Bair Hugger by 3M Company (Saint Paul, MN). Examples of conductive warming can include the apparatus commercially available under the trade designation VitaHeat by VitaHeat Medical (Deer Park, IL).

In at least one embodiment, the apparatus 110 can also configured to receive an input from an external sensor 165 (i.e., not onboard the apparatus 110) and transmit the input received to a medical monitor 175 as discussed further herein. For example, the apparatus 110 apparatus can receive a signal indicative of a physiological indicator of a patient 160 from the sensor 165 and transmit a replica of the signal indicative of the physiological indicator to the medical monitor 175.

The system 100 also includes a patient 160. The patient 160 is generally mammalian, and preferably human, and more preferably, a statistically average adult patient. The term patient generally refers to a class of persons who can have the core body temperature measured (i.e., a patient population).

The system 100 also includes sensors 165. In at least one embodiment, due to a lag time between heat transfer by an apparatus 110 and absorption by the patient 160, detecting heat using physiological indicators from sensors 165 can be useful. For example, the one or more sensors 165 (i.e., attached to or conveying information about the patient) can be configured to read one or more physiological indicators from the patient 160. In at least one embodiment, the sensor 165 can receive a physiological indicator measurement from the patient 160. The physiological indicator can be a physiological response by the patient 160 to the amount of heat provided by the apparatus 110, environment, intrinsically, or combinations thereof. A physiological response can include multiple vital signs of a patient such as respiratory rate, core body temperature, skin temperature, pulse, cardiac electrical activity, skin temperature, oxygen saturation, or combinations thereof.

Sensors 165 may be useful for monitoring physiological indicators of a patient 160. Either one sensor 165 or a plurality of sensors 165 can be used. The sensor 165 will depend on the physiological indicator measured. Examples of sensors 165 can include a (core or skin) temperature sensor, a blood pressure sensor, a heat flux sensor, a SpO2 sensor, a pulse sensor, a moisture sensor, or any combination thereof.

In at least one embodiment, one or more sensors 165 can be placed in any location in or on the patient 160 and sense skin temperature or core temperature. In some embodiments, a zero-flux temperature sensor can be advantageous in measuring core temperature such as those commercially available under the trade designation Bair Hugger by 3M Company. (Saint Paul, MN).

In at least one embodiment, a blood pressure sensor, SpO2 sensor, pulse sensor, or moisture sensor can be used with a temperature sensor to allow a controller to determine whether a patient 160 is likely to sweat or vasodilate as described in pending PCT application PCT/IB2018/054553, which is incorporated by reference. For example, the controller can use a temperature sensor combined with moisture sensor (to detect perspiration) to determine whether the patient 160 is likely to sweat. In another example, a rapid decrease (over a time) in a blood pressure measurement can indicate vasodilation and the lack of body temperature increase can indicate that a patient 160 is likely to sweat.

The system 100 can include a logging unit 170 that is communicatively coupled to the sensor 165. The logging unit 170 can collect data regarding physiological indicators (such as the values) from sensor 165. The logging unit 170 can have an onboard memory, communications, and processor sufficient to store/cache physiological indicator values. The logging unit 170 can be located at a fixed-point relative to the sensor 165. For example, a logging unit 170 can remain in a room while the sensor 165 and patient 160 are mobile.

In at least one embodiment, the apparatus 110 can include the logging unit 170 as an onboard component. For example, the logging unit 170 can receive physiological indicator values from the sensor 165.

The logging unit 170 can be communicatively coupled to a remote computer 185. In at least one embodiment, the logging unit 170 can engage in wireless communication with the sensor 165, the remote computer 185, or combinations thereof. The logging unit 170 can receive the data from the sensor 165 and transmit the data to the remote computer 185.

The system 100 can also include a medical monitor 175 that receives physiological indicator values regarding the patient 160 and displays the physiological indicator values for a user such as a clinician to view. The medical monitor 175 (or patient monitor) can be a device that is configured to receive physiological indicator values from a variety of sensors 165 described herein such as SpO2, electrocardiogram, Blood Pressure, and temperature. Examples of medical monitors are commercially available from General Electric Medical, or Philips.

The system 100 can also include a remote computer 180. The remote computer 180 can have electronic circuitry to interface with the medical monitor 175. For example, the remote computer 180 can have a processor, memory, and communication modules as described herein.

In at least one embodiment, the medical monitor 175 can communicate one or more physiological indicators and the associated values with the remote computer 180, i.e., the remote computer 180 can be communicatively coupled to the medical monitor 175.

In at least one embodiment, the remote computer 180 can be maintained as a separate system from the remote computer 185. For example, the remote computer 180 can be maintained by the medical monitor 175 manufacturer or a medical provider such as a clinic, hospital, an insurance company, or combinations thereof. The remote computer 185 can be maintained by the logging unit 170, or apparatus 110 manufacturer.

The remote computer 180 can store physiological indicator values, and patient data in a datastore 182. The remote computer 180 can be communicatively coupled to a datastore 182 via the network or a direct connection. The datastore 182 may store data in structure or unstructured form. Example datastores may be any one or more of a relational database management system, online analytical processing database, table, or any other suitable structure for storing data.

The datastore 182 can have one or more records which are associated with the patient 160. Any record for the patient can be subject to a record management operation. The record management operation is any operation that changes the record (e.g., creates a new attribute or record, modifies an attribute of an existing record, or deletes an attribute). In at least one embodiment, the record management operation includes modifying a record in the datastore for the patient 160. For example, the record can correspond to physiological indicator obtained from a sensor 165 (e.g., the datastore 182 can include temperature records if the sensor 165 is a temperature sensor).

The system 100 can also include a remote computer 185. The remote computer 185 can be configured like the remote computer 180. The remote computer 185 can also have access to a datastore 187. The records in datastore 187 can differ from that in datastore 182. For example, the records in datastore 182 can have personally identifiable information, or otherwise protected health information whereas the records in datastore 187 are deidentified meaning not being able to be identified or associated with any particular patient 160. In another example, the records in both datastores 182 may be both deidentified but the records in datastore 187 may have apparatus 110 performance data.

Figure 2:
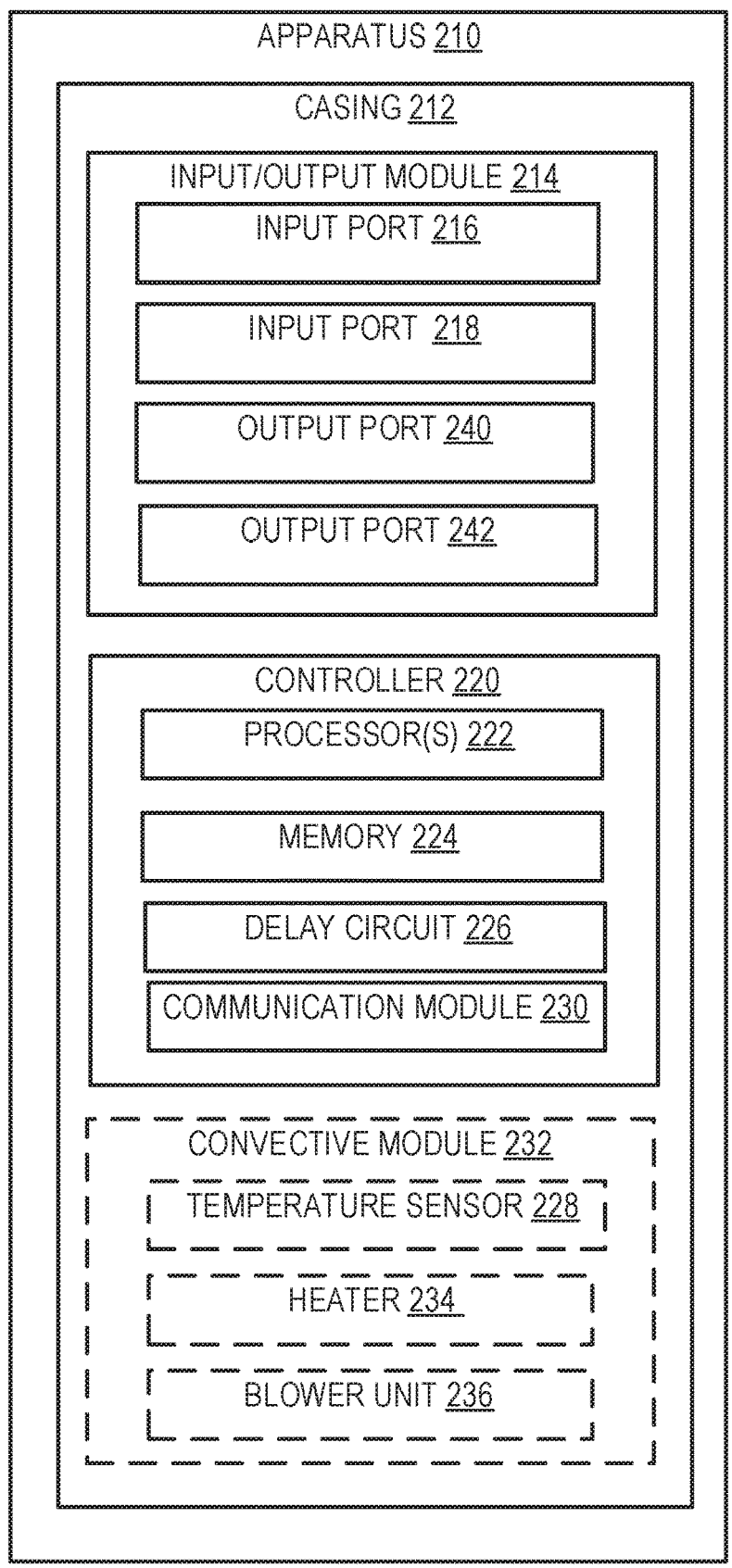
FIG. 2 is a block diagram of an apparatus, according to aspects of the present disclosure.

FIG. 2 illustrates an apparatus 210 that is an embodiment of apparatus 110 in FIG. 1.

The apparatus 210 can include a casing 212 having one or more components including electronic circuitry used to control or monitor the apparatus. In at least one embodiment, the apparatus 210 includes both the Input/Output (IO) module 214, the controller 220, and convective module 232 within the same casing. The casing 212 can have an edge with an outlet opening (formed from a portion of the casing) adapted for coupling to an air hose as shown by commercially available forced air warming units. The casing 212 can also include a housing (not shown) within the casing 212 describing an airflow pathway with an air diffusing outlet (formed from a portion of the housing) proximate to or formed as part of the outlet opening for providing a stream of pressurized air through the outlet opening.

In at least one embodiment, the apparatus 210 can be external to a warming device and attach to the warming device. For example, the IO module 214, and controller 220, can be in a casing 212 and interface/be communicatively coupled with a warming device having a convective module 232 in a different casing. Examples of warming devices are commercially available under the trade designation Bair Hugger by 3M Company (Saint Paul, MN).

The apparatus 210 can also include an input/output (IO) module 214 that receives input from one or more sensors (not shown). The IO module 214 can have at least one input port (e.g., 216, 218) that is configured to electrically couple with the sensor. In at least one embodiment, an input port 216 can be a device with at least one pin or receptacles for receiving elements of a cable (e.g., adapter) from a sensor. For example, if the input port 216 comprises a first pin and the output port 242 comprises a second pin, the first pin is electrically coupled to the second pin. While at least some pins in an input port can receive data (in the form of electrical signals) from a sensor, some pins in an input port can be configured to provide power to an attached sensor.

The input ports can be adjacent to a portion of the casing (or in some cases contacting the casing) and configured to receive a physiological indicator from the sensor. In at least one embodiment, a portion of the input port can be recessed from the surface of the casing 212. In at least one embodiment, a portion of the input port 216 can intersect with a plane of the surface of the casing 212.

The input port 216 can be configured to receive a digital signal or analog signal indicative of a physiological indicator. For example, the input port 216 can receive a resistance value (e.g., in response to a constant voltage) from a sensor, the controller 220 can determine, based on the resistance value, the physiological indicator, and transmit the resistance value through the output port 240. In at least one embodiment, the input port 218 can be multiplexed with the input port 216 such that the data from both the input port 218 and input port 216 can be output on a single output port. In at least one embodiment, the controller 220 and the output port 240 are wired in parallel from the input port 216 such that the data received from the input port 216 is transmitted to the output port 240 and controller 220 at substantial real-time. In at least one embodiment, the input port 216 or output port 240 can also include an amplifier.

The input/output (IO) module 214 can also include input port 218. Input port 218 can receive data from a same or different type of sensor than that received from input port 216. For example, input port 218 can receive EKG data and input port 216 can receive temperature data. In at least one embodiment, the type of signal (analog, digital, radio) can be different between the input port 216 and input port 218. For example, input port 218 can receive a digital signal indicative of a second physiological indicator and the input port 216 receives an analog signal indicative of the first physiological indicator. For example, the input port 216 can receive an analog signal indicative of a second physiological indicator and the input port 218 receives a digital signal indicative of the first physiological indicator. The input port 218 can further comprise a plurality of pins, wherein at least one pin can provide power output to the sensor.

The second physiological indicator can be selected from core body temperature, skin temperature, pulse oximetry, electrical activity of a heart, or combinations thereof. In at least some embodiments, the second physiological indicator is not core body temperature if the first physiological indicator is core body temperature. Although two input ports are shown, the IO module 214 can include a plurality of two or more input ports.

In at least one embodiment, an output port can transmit an exact replica of the signal received by the input port. In at least one embodiment, an output port can be electrically coupled to the input port.

In at least one embodiment, an output port can transmit a non-exact replica of the signal received by the input port. The signal from an input port can be converted from one value type to another value type. For example, the input port 216 can receive the first physiological indicator as a digital signal but transmit the first physiological indicator through the output port 240 as an analog value.

One or more output ports that are paired with one or more input ports from the IO module 214. For example, output port 240 can be paired with input port 216 such that a signal from input port 216 is replicated (either digital or analog) at output port 240. The apparatus 210 can determine a first physiological indicator and transmit the first physiological indicator through an output port nearly simultaneously as a replica of a signal received.

Output port 242 can be paired with input port 218. For example, input port 216 can also include a first pin and the output port 242 comprises a second pin, the first pin is electrically coupled to the second pin.

In at least one embodiment, there may be one or more pairs of input ports and output ports configured to communicatively couple to an external warming device having a convective module 232 as described herein.

The apparatus 210 can also include a controller 220. The controller 220 can have various circuitry described herein such as one or more processors 222, memory 224, and a communication module 230 to interact with the convective module 232 and remote computer, and/or control device settings of a convective module 232.

The controller 220 can be communicatively coupled to the IO module 214, the convective module 232, and/or a remote computer. The operation of the controller 220 can be described further herein.

The controller 220 can also include a delay circuit 226 which can introduce a time delay between an output port and an input port. The time delay can occur to synchronize a frequency of the values received at the input port with the expected frequency of values at a medical monitor. For example, the input port 216 can receive SPO2 values at 100 samples per minute but the medical monitor is expecting 60 samples per minute. Thus, the delay circuit 226 can delay the SPO2 values and page the excess values in memory 224.

The controller 220 can also include one or more communication modules 230. The one or more communication modules 230 can communicate with other elements of the system described in FIG. 1, e.g., the remote computer 185, sensors 165, medical monitor 175, or combinations thereof.

If within the casing 212 as described herein, the apparatus 210 may also include a convective module 232. Components of the convective modules 232 can be similar to those found in warming units commercially available by 3M Company under the trade designation, Bair Hugger or Bair Paws. The convective module 232 can be disposed in the housing and the outlet opening via the airflow pathway. The convective module can also include a heater 234 which uses heat to heat the surrounding air, and a blower unit 236 to propagate air passed through the heater 234 onto a patient. Both the heater 234 and the blower unit 236 can function to provide warmed air at a certain temperature and flow rate to the patient.

The temperature sensor 228 can communicatively couple to the controller 220. The temperature sensor 228 can be disposed in the airflow pathway within the casing 212 (thus, fluidically coupled to the airflow pathway) and is configured to receive an airflow temperature. The controller 220 can adjust one or more settings of the heater 234 or blower unit 236 to maintain a propagated air at a specific temperature.

In at least one embodiment, the apparatus can perform one or more aspects of method 300. Although the apparatus is described as performing the method 300, aspects of the method 300 can also be performed by the logging unit in parallel or independently. Method 300 can begin at block 310. In block 310, a user can insert a sensor interface (i.e., a portion of the sensor) into a port in the apparatus physically adapted to receive the sensor interface. For example, the sensor interface for a temperature sensor can be a male, YSI-compatible connector (e.g., YSI-400 and YSI-700 and the apparatus input port can be a female, YSI-compatible receiver.

In at least one embodiment, block 310 can be optional as the communication between the sensor and the apparatus can be wireless and rely on a pairing arrangement such as a handshake which establishes the protocols of a communication link at the start of communication before full communication begins.

In block 312, the apparatus can receive a signal indicative of a physiological indicator value from the sensor via an input port. In at least one embodiment, the receipt of the physiological indicator value can occur in response to inserting the sensor interface into the apparatus. For example, the sensor can continuously transmit values which are received by the apparatus and analyzed. The signal can be in analog or digital and in a processed or raw state. In at least one embodiment, block 312 can occur after block 314. For example, the apparatus can receive physiological indicator values only after determining whether the sensor is supported.

In block 314, the apparatus can determine whether the sensor is supported. In at least one embodiment, the sensor can provide an identification signal to the apparatus. For example, the sensor can provide a unique code unique to the sensor that indicates the identity of the sensor which can be confirmed via an on-board lookup table. The apparatus can then determine whether the sensor is among the list of those sensors supported. The apparatus can also receive an authentication signal from a unique authentication chip present in the sensor itself.

In at least one embodiment, the apparatus can also determine whether the sensor is supported based on the physiological parameter value alone. For example, if the sensor is a core body temperature sensor, then a physiological parameter value can be any value that corresponds to a body temperature. If the value received is 1, then this value does not correspond to a physiological body temperature of the patient. Further, the value of 1 cannot correspond to a physiological blood pressure value, or a pulse oximetry. However, the value of 1 can correspond to a millivolt potential received from an EKG sensor. Thus, the apparatus can determine that the sensor is an EKG sensor. Timing information can also be obtained from the physiological parameter values to indicate whether the frequency of physiological indicator values is supported.

In at least one embodiment, a sensor interface can be modified to provide mechanical obstructions to non-supported sensors. For example, a sensor may be supported by the apparatus if the sensor interface physically fits into the input port and contacts all the pins of the input port.

If the sensor is supported, then the apparatus can determine a sensor type in block 316. As described herein, the sensor type can be can be based on a signal received by the apparatus. The sensor type can also be based on the input port that is receiving the physiological indicator. For example, if a first input port is configured to be the port for receiving a core temperature, and a second input port is the port for receiving an EKG, then values received from the first input port necessarily correspond to a core temperature sensor and values received from the second input port necessarily correspond to an EKG sensor. Thus, if a pressure switch indicates that a pin is inserted into the second input port, then the controller can determine that the EKG sensor is present.

In block 320, the apparatus can determine a physiological indicator from the sensor input port. For example, the signal received from the input port can be analog and may need to be converted to digital to interpret the value from the signal received. In at least one embodiment, block 320 can be optional depending on the type of signal received in block 312.

In block 322, the apparatus can perform at least one operation in response to determining the physiological indicator values. In at least one embodiment, the apparatus can control a portion of the convective module based on the physiological indicator. For example, the apparatus can determine that the sensor type is a core body temperature sensor and increase or decrease the temperature of the heater or flowrate of the blower unit based on a core body temperature physiological indicator and the airflow temperature of the convective module. In another example, the apparatus can use the physiological indicator to control one or more settings of the apparatus as described in PCT/IB2018/054553, filed 20 Jun. 2018, which is incorporated by reference. For example, a heating level of a heater or airflow of a blower unit of the apparatus control the heater or blower unit based on receiving the airflow temperature from the airflow temperature sensor and the core body temperature of a patient, or between a fingertip and forearm skin temperature difference.

In at least one embodiment, the apparatus can also transmit data from the input port through an output port leading to the medical monitor as in block 328. For example, the apparatus can transmit the physiological indicator though the sensor output port. In at least one embodiment, a single output port can transmit to multiple input ports on a patient monitor. For example, a cable leading to the input ports can be split and multiplexed based on timing of the output from the apparatus. For example, a switch can be configured to select between a few EKG values, a temperature value, and a pulse oximetry value in a round-robin format.

In at least one embodiment, the operation can also include saving the data locally in the memory for later retrieval. For example, data saved locally may be useful to determine trends to further control the convective module. For example, a rising core body temperature may be an indication to reduce the heating capacity of the convective module.

In at least one embodiment, performing an operation can also include communicating the data with a remote computer. Communication with a remote computer can be instantaneous or with a delay. The remote computer can further analyze multiple sets of physiological indicators to determine trends or specific data for a particular patient.

The operations that may be performed can differ depending on whether the sensor is supported in block 314. For example, if the sensor is supported by the apparatus (e.g., by being authenticated or being of a sensor type), then the apparatus may perform some operations based on the sensor is supported.

If the sensor is not supported by the apparatus (e.g., not authenticated), then the apparatus can transmit the signal from either the first or second input port (e.g., rebroadcast the signal) via the output port without controlling one or more settings of the apparatus. The controller can also communicate to a user that the sensor is not supported by the apparatus in block 324 (which can also be optional)

In at least one embodiment, the apparatus can optionally communicate the status (e.g., whether the sensor is supported) to the user visually or auditorily. For example, the apparatus can alert a user that the device is not supported for automated setting adjustments to the convective module.

Further, the apparatus can communicate that pass-thru transmission of the signal is enabled even though the automated adjustments to one or more settings of the convective apparatus are not supported.

In block 326 the apparatus can optionally analyze data integrity of the signal. Even though depicted as occurring after block 324, block 326 can occur at any point such as after or currently with block 320. By analyzing the data integrity, the apparatus can determine whether to transmit data to the patient monitor as described further herein.

Figure 4:
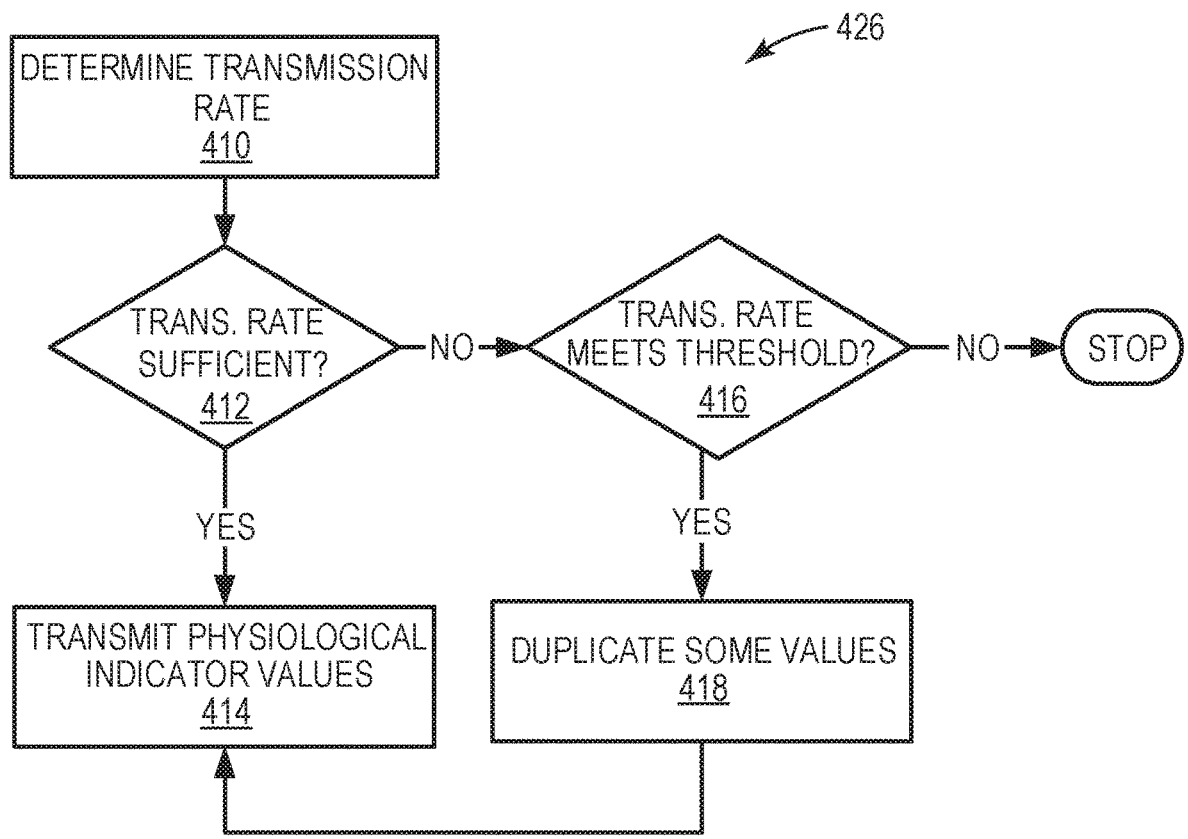
FIG. 4 is a flowchart of a method of analyzing data integrity of a signal indicative of a physiological indicator, according to aspects of the present disclosure.

In block 328, the apparatus can transmit the signal received from the input port through the output port as a replica of the signal. FIG. 4. In at least one embodiment, the signal can be conditioned to be transmitted to the patient monitor (e.g., amplified, noise reduction, converted to digital values, etc. prior to being transmitted).

Figure 3:
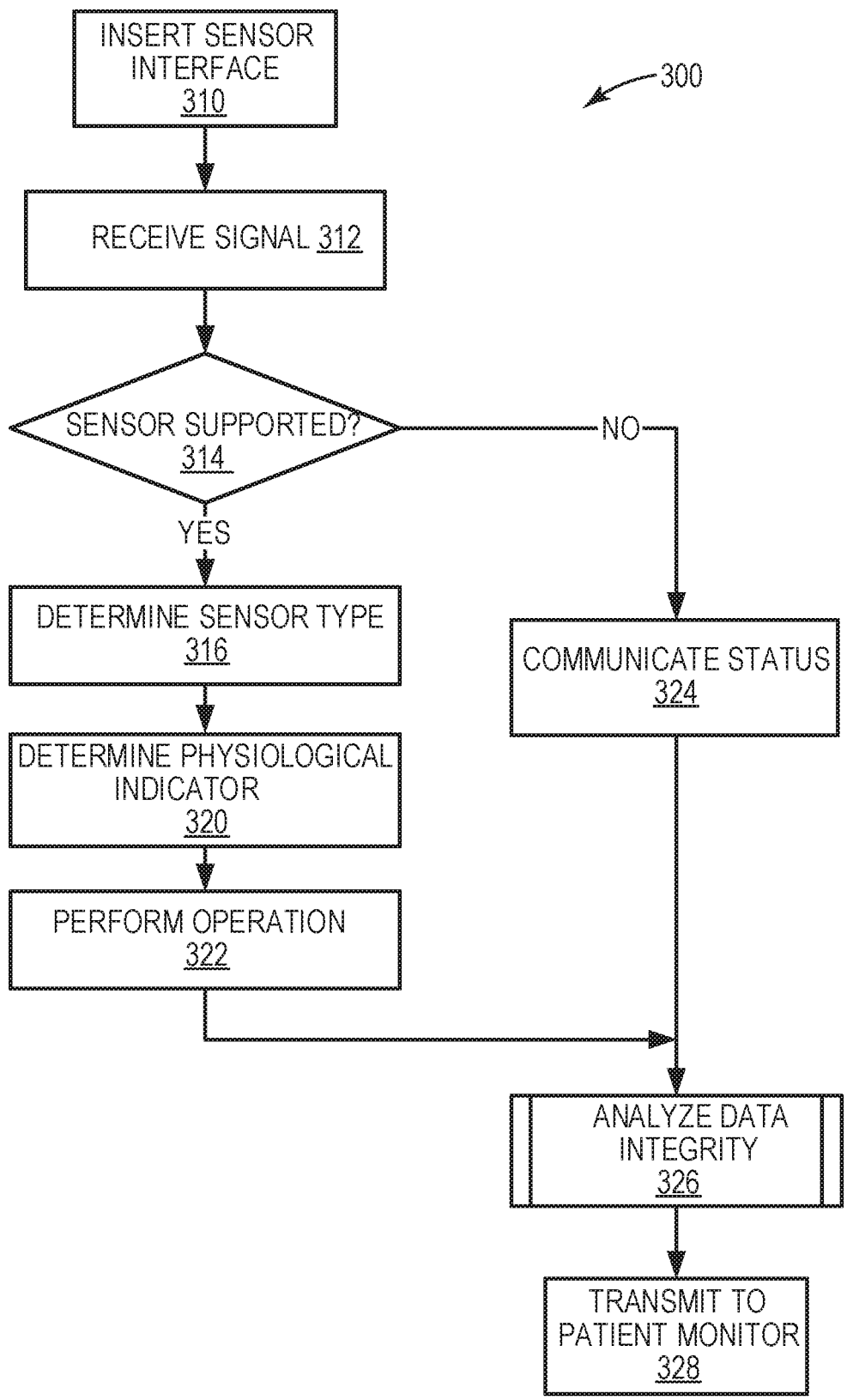
FIG. 3 is a flowchart of a method of using data from a sensor, according to aspects of the present disclosure.

FIG. 4 illustrates a method 426 for analyzing data integrity as shown in block 326 in FIG. 3.

The method 426 can begin at block 410. In block 410, the apparatus can determine a transmission rate of the incoming data at an input port. The transmission rate can be based on the number of physiological indicator values that occur in a set time period and can differ depending on the physiological indicator received. For example, the core body temperature (about 1 to 2 samples per minute) has a low transmission rate relative to EKG (hundreds of samples per minute) and SPO2. The transmission rate can be based off a rolling average such as from a stream of data signals.

Once determined, in block 412, the apparatus can determine whether the transmission rate is sufficient for the sensor type. Each sensor type can have a threshold value representing a minimum transmission rate necessary to indicate whether the data stream would yield an informative condition about the patient. The sufficiency of the transmission rate can depend on the type of physiological indicator. For example, a transmission rate of 1 value per minute may be sufficient for a temperature value but not as an EKG amplitude value.

If the transmission rate is sufficient, then, in block 414, the apparatus can transmit the data stream via the output port as described in block 328 in FIG. 3. If the transmission rate is not sufficient, then the apparatus can determine whether sampling rate meets a duplication threshold in block 416.

The duplication threshold can be a transmission rate where at least some of the physiological indicator values can be duplicated to increase the transmission rate. The duplication threshold can vary depending on the type of data received from the sensor. For example, below 50 values per minute may not be duplicated for an EKG but some values between 70 and 80 values per minute may be duplicated. The duplication threshold can be set such that duplication does not affect the trends reflective of the physiological indicator. In at least one embodiment, the duplication threshold can reflect a number or percentage of values that can be duplicated within a set such that the trend of the physiological indicator is unaffected.

In block 418, the apparatus can duplicate at least some of the physiological indicator values. The duplication can be responsive to the incoming signal. For example, the duplication can occur based on a time. e.g., every ten seconds, duplicate preceding physiological indicator value if no physiological indicator value is received within the ten second timeslot. In another example, the duplication can be based on a number of values received, e.g., every 2 values, duplicate the preceding physiological indicator value.

Figure 5:
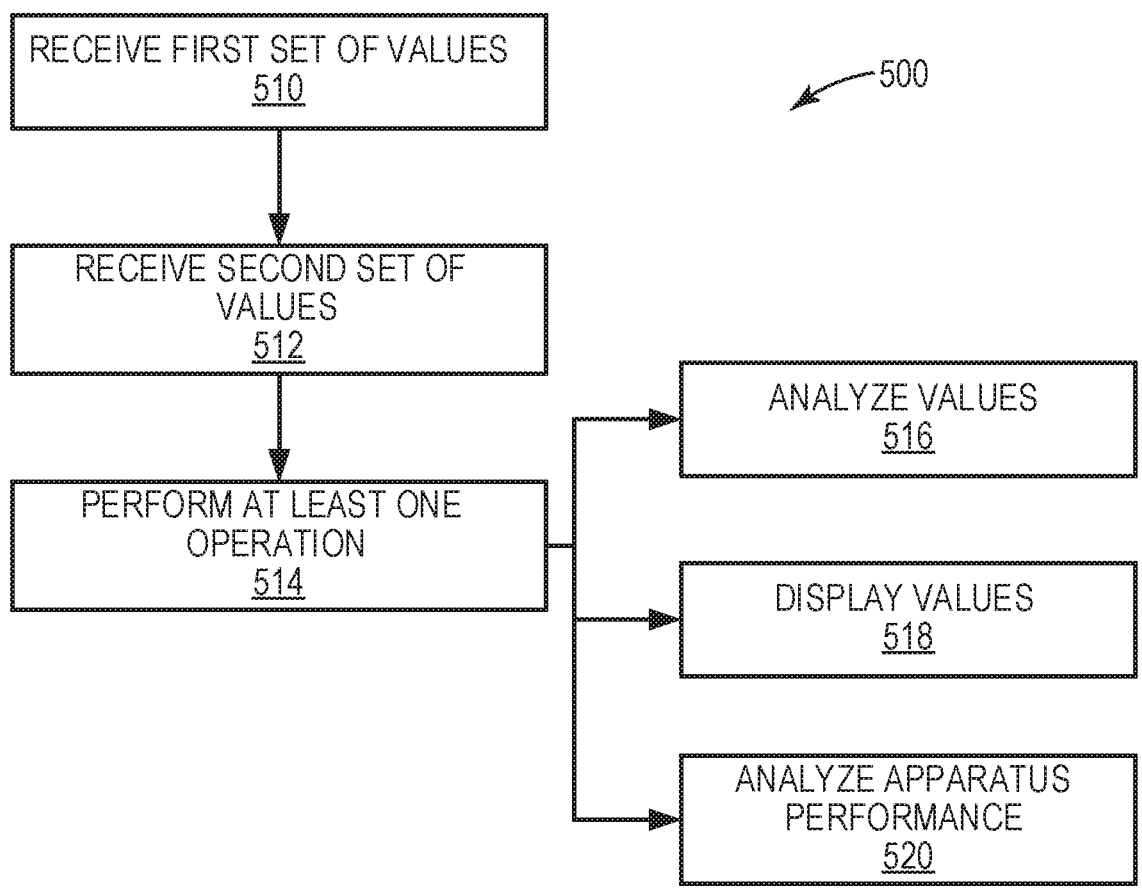
FIG. 5 is a flowchart of a method of transmitting physiological indicator values, according to aspects of the present disclosure.

FIG. 5 illustrates a method 500 that may be performed by a remote computer that is communicatively coupled to the apparatus. The method 500 can begin at block 510.

In block 510, the remote computer can be configured to receive a first set of physiological indicator values. The first set of physiological indicator values can be transmitted by the apparatus, a logging unit communicatively coupled to the sensor, the sensor itself, or combinations thereof. The first set of physiological indicator values can correspond to a patient, a location, or an instance where physiological indicator values are obtained.

In block 512, the remote computer can be configured to receive a second set of physiological indicator values. The second set of physiological indicator values can correspond to a second patient, a second location, or a second instance. In at least one embodiment, the second set of physiological indicator values can be different from the first set. For example, if 5 values are in the first set, then the second set can have a different combination than the first set. In at least one embodiment, at least some of the values can be shared between the first set and the second set to indicate a time delay.

In block 514, the remote computer can perform at least one operation. Examples of various operation include blocks 516-520.

In block 516, the remote computer can analyze the first and second set of physiological values. For example, the remote computer can perform statistical analysis to track a physiological indicator of a patient based on location. For example, the remote computer can isolate core body temperatures of a patient in pre-op, surgical, and post-op regions of a hospital. This data can be combined with the data from the apparatus to determine effectiveness of the convective module. For example, poor performance of a blower unit can cause core body temperature to drop leading to conclusions about apparatus performance.

Various analysis of data can also occur such as determining the severity of hypothermia by analyzing an area under a temperature curve of a patient, detection of prewarming, and calculating a duration of a time gap between prewarming and warming in an operating room. The data could be used to improve the warming process in the hospital.

In block 518, the remote computer can display the first and second set of physiological indicator values. In at least one embodiment, the first and second set can be part of the same instance. For example, a patient's core body temperature and EKG chart can be displayed on the same graph to determine if there is a relationship between two different physiological parameters. Values from the first set can be visually distinguished from the second set on the same graph through color changes or other visual identifications.

In block 520, the remote computer can analyze apparatus performance which can be further described herein. For example, the apparatus can receive apparatus device settings and performance data such as data resulting from the convective module (e.g., airflow temperature data, airflow rate data, or run times of the motor) and analyze the device settings and performance data.

Figure 6:
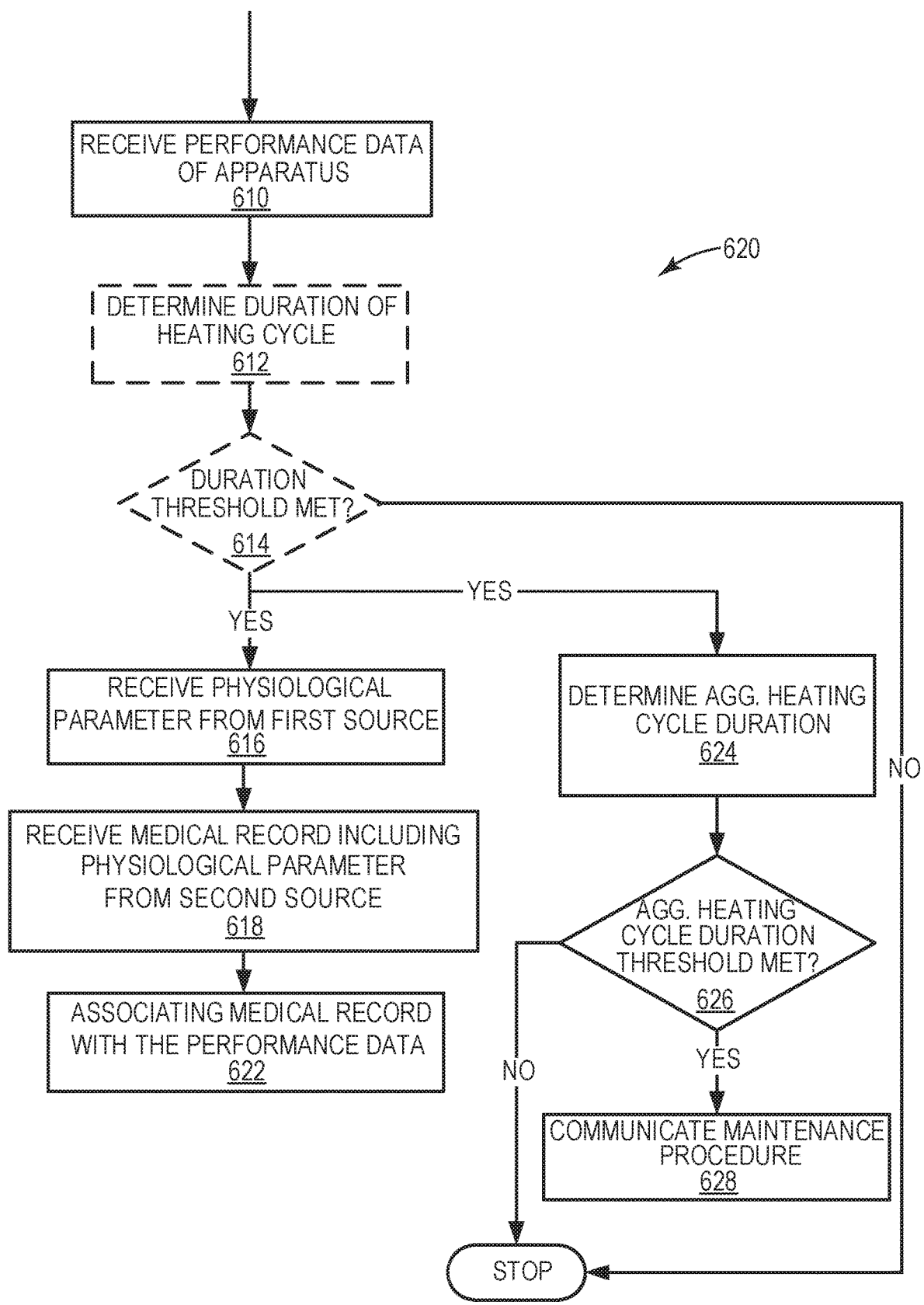
FIG. 6 is a flowchart of a method of analyzing apparatus performance, according to aspects of the present disclosure.

FIG. 6 illustrates a flowchart of a method 620 illustrating a remote computer analyzing performance data of the apparatus. Method 620 can be an embodiment of block 520 in FIG. 5.

Method 620 can begin in block 610. In block 610, the remote computer can receive performance data from the apparatus. The performance data is generally obtained from a convective module but can be obtained from a conductive module or infrared module if the heat source is primarily conductive or infrared. The performance data can include temperature data from the internal airflow temperature sensor, the blower unit air speed, or the time of either temperature or air speed.

In block 612, the remote computer can optionally determine duration of the heating cycle from the performance data. For example, if the blower unit is activated, then the remote computer can determine the total amount of time that the blower unit is activated (minus any time that the blower unit is deactivated) as the duration. In a conductive heating system, the duration can be the total amount of time that the heater is activated.

In block 614, the remote computer can optionally determine whether duration of the heating cycle meets a threshold, i.e., whether apparatus completed a full warming cycle on a patient. A full warming cycle can be based on an amount of time to maintain normothermia in a patient, generally, for the duration of a surgical procedure. For example, if the total time activated is only 4 minutes, then it is unlikely to be equivalent to a full warming cycle. Thus, the duration threshold can be based on a setpoint for a surgical procedure.

In at least one embodiment, the remote computer can look for patterns of use that indicate that the warming device was turned on. For example, a deactivation or ambient setting (where the heater is off, but the blower unit is activated) can indicate a definitive stopping point for a warming cycle. Also, constant changes of device settings (increasing decreasing heater temperatures) can indicate that a patient is present versus long periods of inactivity. In at least one embodiment, the duration of the heating cycle can be determined by the presence of data from the sensors (such as a temperature reading) and the performance data from the apparatus. Once duration meets a threshold, a number of actions can occur. In at least one embodiment, if the duration does not meet the threshold, then the method 600 can stop and the duration can be logged.

For example, in blocks 616 to 622, the remote computer can match medical records obtained from another remote computer to a patient instance based on one or more performance data of the apparatus (e.g., performance data related to determining a duration time). As described, blocks 616 to 622 can describe a general method to identify a medical record of a patient by physiological data if no patient identification is provided by the apparatus.

In block 616, the remote computer receives a physiological indicator from the first source. The first source can be from the apparatus. In at least one embodiment, performance data and physiological indicator data from the apparatus is deidentified, i.e., pseudominized, meaning that data in the data set cannot be attributed to the patient such as a patient identifier. However, it may be possible to associate the performance data with an individual patient if access to a medical record is later given.

In block 618, the remote computer receives a medical record that includes the physiological indicator from the second source. The second source can be from a medical monitor or a medical database. For example, if the physiological indicator is EKG, then the subset of EKG values may be meaningless on its own. However, the remote computer can compare the subset of EKG values against the entire range of EKG values for multiple patient instances obtained from medical records. Once a statistically relevant match occurs between the subset of EKG values and EKG values for a patient instance, then the performance data of the apparatus/duration can be associated with that patient instance in block 622 in order to further analyze functions of the apparatus and a physiological response of the patient to the apparatus. For example, if a performance setting of 900 W from the apparatus exists, with a patient body mass index of 23, then the remote computer can determine the effectiveness of thermal energy transfer for patients with body mass indexes of 23 across populations of patients.

In blocks 624 to 628, the remote computer can analyze performance data to determine a maintenance procedure needs to occur.

In block 624, the remote computer can determine aggregate heating cycle duration based on multiple durations for multiple instances of patients. For example, a first patient may activate the convective module for 3 hours and a second patient may activate the convective module for 4 hours. Thus, the aggregate heating cycle duration is 7 hours.

In block 626, the remote computer can determine whether the aggregate heating cycle duration threshold is met by the aggregate heating cycle duration. The aggregate heating cycle duration threshold can be based on expected performance of the various components of the apparatus. For example, if a blower unit motor needs to be replaced after 200 hours of runtime, then the aggregate heating cycle duration threshold can be set to 200 hours.

In block 628, the remote computer can communicate maintenance procedure recommendation to user. For example, the remote computer can send a message directly to an administrative user to communicate the type of maintenance procedure to be performed. The remote computer can also cause the apparatus to display a message indicating that a component needs to be serviced.

Figure 7:
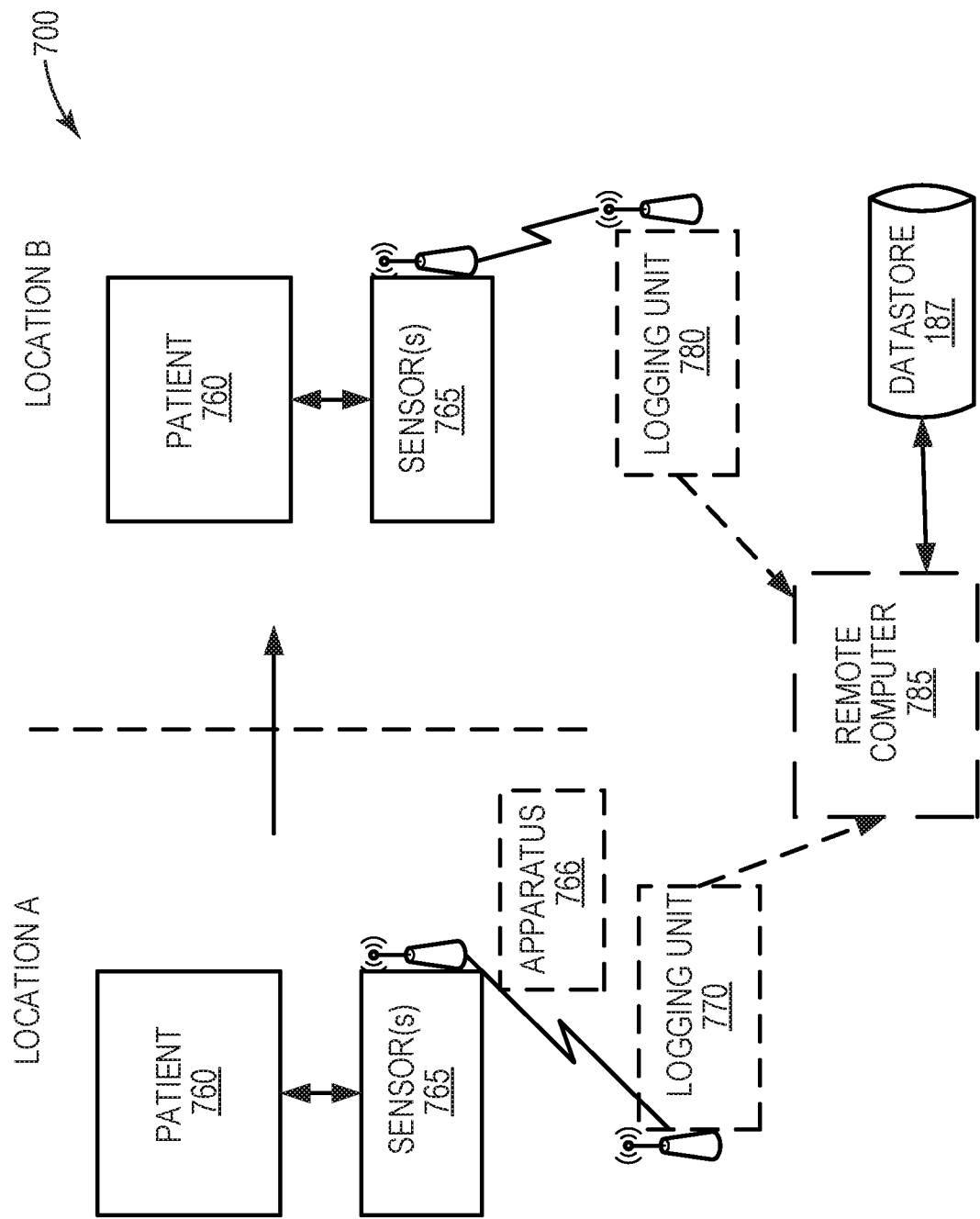
FIG. 7 is a block diagram of a system including a logging unit, according to aspects of the present disclosure.

FIG. 7 illustrates a block diagram of a system 700 for using a sensor 765 to provide data to a remote computer 785. The system 700 includes a patient 760 as described herein. A sensor 765 is communicatively coupled to the patient 760 such that the sensor 765 reads one or more physiological indicators from the patient 760. The sensor 765 is described further herein.

The system 700 also includes an optional logging unit 770. As discussed herein, the logging unit 770 can communicate with the sensor 765 and the remote computer 785 and may also be a part of the apparatus. The logging unit 770 can be fixed relative to the patient. For example, the logging unit 770 can be located in and associated with location A.

In at least one embodiment, the logging unit 770 can have information about the location A and adds this info to the record that is transmitted to the remote computer 785. In at least one embodiment, the logging unit 770 can modify the record and add an ID of the logging unit 770. The remote computer 785 can add the location info associated with the logging unit ID.

The physiological indicator values from the sensor 765 can be transmitted from the logging unit 770 with a location stamp indicating location A to the remote computer 785 and stored in the records 187. As the patient 760 and sensor 765 is moved from location A to location B, the sensor 765 can switch from transmitting from the logging unit 770 to the logging unit 780. The physiological indicator values from the sensor 765 can be transmitted from the logging unit 780 to the remote computer 785 indicating location B and stored in the records 187. In at least one embodiment, location A can indicate a pre-surgical area and location B can represent a surgical area. Thus, the data collected from the sensor 765 can be collected from the logging units and the remote computer 785 can analyze trends related to pre-warming effectiveness of the apparatus (with respect to the patient) and surgical effectiveness (with respect to the patient).

In at least one embodiment, the sensor 765 can be communicative coupled to either the logging unit 770 or the apparatus 766 described herein. The sensor 765 can be communicatively coupled to the controller of the apparatus 766 and the apparatus 766 can be communicatively coupled to the logging unit 770. Thus, the apparatus 766 can act as an intermediary between the sensor 765 (wired connection) and the logging unit 770 (wireless communication or on-board).

Figure 8:
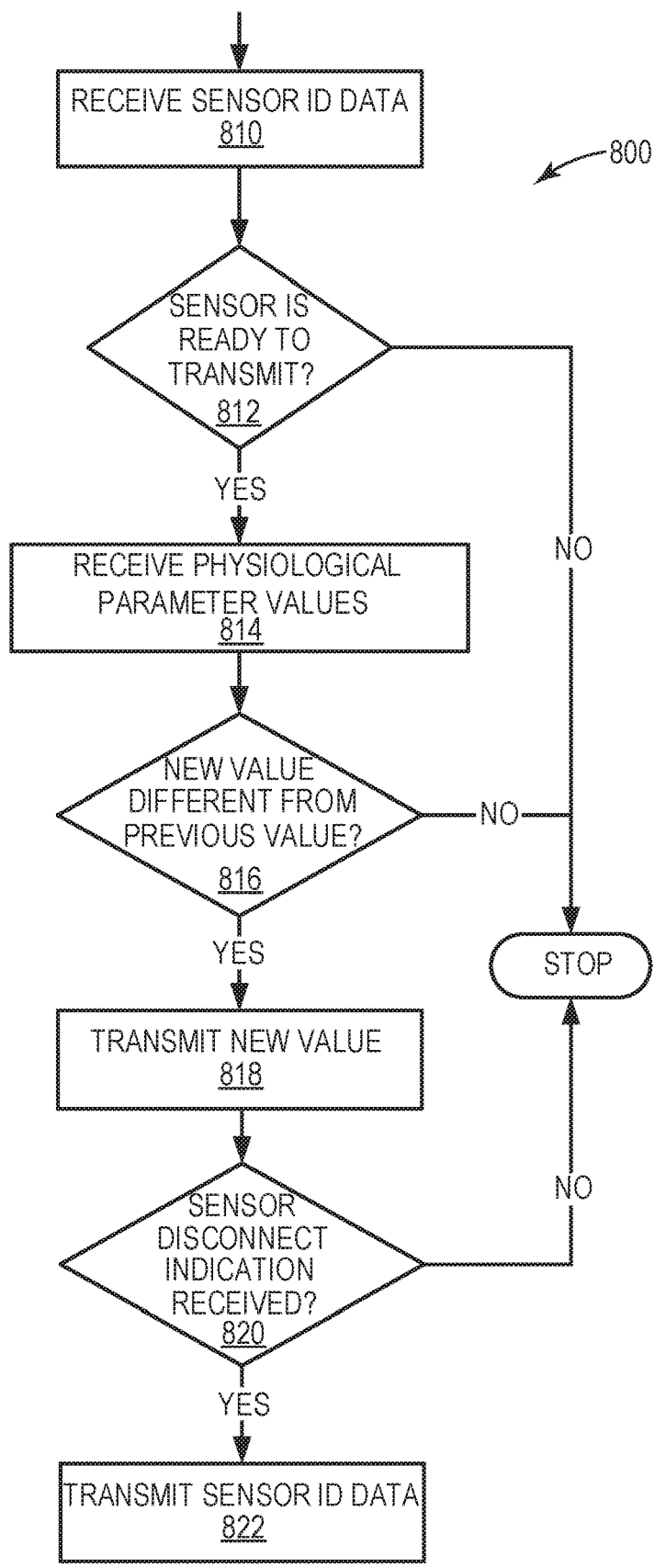
FIG. 8 is a flowchart of a method of transmitting data from a sensor, according to aspects of the present disclosure.

FIG. 8 illustrates a method 800 of the logging unit transmitting data received. The method 800 can begin at block 810.

In block 810, the logging unit can receive sensor ID data from the sensor. The sensor ID data can be an identification of the sensor. For example, sensor ID data includes serial number, IP address, timestamp, MAC address, etc.

In block 812, the logging unit can determine whether the sensor is ready to transmit. For example, the logging unit can determine whether the sensor is attached to patient, e.g., the sensor can be based on a proximity sensor within the sensor. In another example, the logging unit determines whether sensor has equilibrated with respect to ZHF temperature sensors having a heater.

In at least one embodiment, block 812 can be optional as the sensor can automatically transmit data.

In block 814, the logging unit can receive physiological indicator values from the sensor. The physiological indicator values can also include the type of physiological indicator meant to be received by the sensor along with a time that the value is received.

In block 816, the logging unit can determine whether the new physiological indicator value is different from the last received physiological indicator value. For example, if multiple duplicate values are received, the non-duplicative physiological indicator value can be stored for later transmission or can be associated with a single repeat character to indicate the physiological indicator value as part of a data compression scheme.

In block 818, the logging unit can optionally transmit the new value to the remote computer. The transmission can occur continuously as a stream of data or the logging unit can save at least some of the data to be transmitted at a later time. The transmission can be over the network or wireless communication.

As part of an ongoing operation, in block 820, the logging unit can receive a sensor disconnect indication. For example, if the sensor is out of range of the logging unit, the transmission signal may become too weak to maintain a connection and a sensor disconnect indication. If a sensor disconnect indication is received, then in block 822, the logging unit can transmit the sensor ID data to the remote computer.

FIG. 9 shows a detailed example of various devices that may be configured to execute program code to practice some examples in accordance with the current disclosure. For example, computing device 900 may be a computing device that performs any of the techniques described herein, e.g., the controller of the apparatus or the remote computer. In the example illustrated in FIG. 9, a computing device 900 includes a processor 910 that is operable to execute program instructions or software, causing the computer to perform various methods or tasks. Processor 910 is coupled via bus 920 to a memory 930, which is used to store information such as program instructions and other data while the computer is in operation. A storage device 940, such as a hard disk drive, nonvolatile memory, or other non-transient storage device stores information such as program instructions, data files of the multidimensional data and the reduced data set, and other information. The computer also includes various input-output elements 950, including parallel or serial ports, USB, Firewire or IEEE 1394, Ethernet, and other such ports to connect the computer to external device such as a printer, video camera, surveillance equipment or the like. Other input-output elements may include wireless communication interfaces such as Bluetooth™, Wi-Fi™, and cellular data networks.

Various examples and implementations will be described in detail. These examples should not be construed as limiting the scope of the present disclosure in any manner, and changes and modifications may be made without departing from the spirit and scope of the disclosure. Further, only some end uses have been discussed herein, but end uses not specifically described herein are included within the scope of the present disclosure. As such, the scope of the present disclosure should be determined only by the claims.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multithreaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Those having skill in the art will appreciate that many changes may be made to the details of the above-described examples and implementations without departing from the underlying principles thereof. The scope of the present disclosure should, therefore, be determined only by the following claims.

LIST OF ILLUSTRATIVE EMBODIMENTS

1. An apparatus for providing pressurized, thermally conditioned air to an air hose, comprising:
 a casing;
 a housing in the casing describing an airflow pathway with an air diffusing outlet proximate to an outlet opening for providing a stream of pressurized air through the outlet opening;
 a convective module disposed in the housing and the outlet opening via the airflow pathway;
 a first sensor input port adjacent to a portion of the casing and configured to receive a signal indicative of a first physiological indicator;
 a first sensor output port adjacent to a portion of the casing and configured to transmit the signal indicative of the first physiological indicator;
 a controller communicatively coupled to the first sensor input port, the first sensor output port, the convective module, the controller comprising one or more computer processors and a memory comprising instructions that when executed by the one or more computer processors cause the one or more computer processors to:
  determine a first physiological indicator value from the first sensor input port;
  perform at least one operation in response to the determination of the first physiological indicator value.
1a. The apparatus of embodiment 1, wherein the apparatus is a warming apparatus configured to provide warmed air to an air hose.
2. The apparatus of embodiment 1, wherein to perform at least one operation comprises transmitting the first physiological indicator though the first sensor output port.
3. The apparatus of embodiment 1 or 2, wherein perform at least one operation comprises controlling a portion of the convective module based on the first physiological indicator.
4. The apparatus of any of embodiments 1 to 3, further comprising: an airflow temperature sensor fluidically coupled to the airflow pathway configured to receive an airflow temperature.
5. The apparatus of embodiment 4, wherein the controller comprises a memory comprising instructions that when executed by the one or more computer processors cause the one or more computer processors to control the convective module based on receiving the airflow temperature from the airflow temperature sensor.
6. The apparatus of embodiment 1, wherein the first physiological indicator is selected from core body temperature, skin temperature, pulse oximetry, electrical activity of a heart, or combinations thereof.
7. The apparatus of embodiment 6, wherein the first physiological indicator is core body temperature of a patient.
8. The apparatus of any of embodiments 1 to 7, wherein the first sensor input port is configured to receive a digital signal indicative of the first physiological indicator.
9. The apparatus of embodiment 4, wherein the first temperature is received digitally.
10. The apparatus of embodiment 9, wherein the controller comprises a memory comprising instructions that when executed by the one or more computer processors cause the one or more computer processors to determine a first physiological indicator by receiving the first physiological indicator as a digital value; and transmitting the first physiological indicator as an analog value.
11. The apparatus of any of embodiments 1 to 6, wherein the first sensor input port is configured to receive an analog signal indicative of the first physiological indicator.
12. The apparatus of embodiment 11, wherein the first sensor input port is configured to receive a first resistance value from a first sensor.
13. The apparatus of embodiment 12, wherein the controller comprises a memory comprising instructions that when executed by the one or more computer processors cause the one or more computer processors to:
 receive the first resistance value from the first sensor;
 determine, based on the first resistance value, the first physiological indicator.
14. The apparatus of any of embodiments 1 to 13, wherein the controller comprises a memory comprising instructions that when executed by the one or more computer processors cause the one or more computer processors to:

transmit the first resistance value through the first sensor output port.
15. The apparatus of any of embodiments 1 to 10, wherein the controller is multiplexed with the first sensor input port.
16. The apparatus of any of embodiments 1 to 15, wherein the controller and the first sensor output port are wired in parallel from the first sensor input port.
17. The apparatus of embodiment 16, wherein the controller comprises a memory comprising instructions that when executed by the one or more computer processors cause the one or more computer processors to determine a first physiological indicator and transmit the first physiological indicator nearly simultaneously as a replica of a signal received.
18. The apparatus of any of embodiments 1 to 17, further including power conversion apparatus for converting AC power for use by the heater.
19. The apparatus of any of embodiments 1 to 18, further including an intake opening in the end for admitting air into the casing.
20. The apparatus of any of embodiments 4 to 19, wherein the controller comprises a memory comprising instructions that when executed by the one or more computer processors cause the one or more computer processors to increase the temperature of the heater or flowrate of the blower unit based on a first physiological indicator and the airflow temperature.
21. The apparatus of any of embodiments 1 to 20, wherein the controller comprises a memory comprising instructions that when executed by the one or more computer processors cause the one or more computer processors to increase or decrease the temperature of the heater or the flowrate of the blower unit based on the first temperature being within a body heat threshold.
22. The apparatus of embodiment 21, wherein the body heat threshold is between 36 and 38 degrees C. (inclusive).
23. The apparatus of any of embodiments 1 to 22, wherein the first sensor input port comprises a first pin and the first sensor output port comprise a second pin, the first pin is electrically coupled to the second pin.
24. The apparatus of any of embodiments 1 to 22, further comprising a second sensor input port and a second sensor output port.
25. The apparatus of embodiment 24, wherein the second sensor input port comprises a first pin and the second sensor output port comprise a second pin, the first pin is electrically coupled to the second pin.
26. The apparatus of embodiment 24, wherein the second sensor input port receives a digital signal indicative of a second physiological indicator and the first sensor input port receives an analog signal indicative of the first physiological indicator.
27. The apparatus of embodiment 24, wherein the second sensor input port receives an analog signal indicative of a second physiological indicator and the first sensor input port receives a digital signal indicative of the first physiological indicator.
28. The apparatus of any of embodiments 26 to 27, wherein the second physiological indicator is selected from core body temperature, skin temperature, pulse oximetry, electrical activity of a heart, or combinations thereof.
29. The apparatus of embodiment 28, wherein the second physiological indicator is not core body temperature.
30. The apparatus of any of embodiments 1 to 29, wherein the controller comprises a delay circuit, wherein the delay circuit is configured to delay a signal from the first sensor output port or the second sensor output port.
31. The apparatus of any of embodiments 1 to 30, wherein the controller comprises an authentication circuit configured to receive an identification signal from the first or the second sensor input port unique to the first or the second sensor, determine a sensor type from the identification signal, perform at least one operation responsive to the sensor type.
32. The apparatus of any of embodiments 1 to 31, wherein the controller comprises a memory comprising instructions that when executed by the one or more computer processors cause the one or more computer processors to perform at least one operation by determining that the sensor type is a core body temperature sensor, and increasing or decreasing the temperature of the heater or flowrate of the blower unit based on a first physiological indicator and the airflow temperature in response to the core body temperature sensor.
33. The apparatus of embodiment 32, wherein the controller comprises a memory comprising instructions that when executed by the one or more computer processors cause the one or more computer processors to perform at least one operation by determining that the sensor type is not compatible with the apparatus and transmitting the signal from the first or second sensor without controlling the heater or blower unit.
34. The apparatus of embodiment 33, wherein the controller comprises a memory comprising instructions that when executed by the one or more computer processors cause the one or more computer processors to also communicate compatibility status regarding the sensor to the user.
35. A system, comprising:
the apparatus of any of embodiments 1 to 31;
a first sensor configured to measure a first physiological indicator of a patient.
36. The system of embodiment 35, further comprising a second sensor configured to measure a second physiological indicator of a patient.
37. The system of embodiment 35 or 36, wherein the first physiological indicator is core body temperature, the first sensor comprising a core body temperature monitor configured to electrically couple to the first sensor input port.
38. The system of any of embodiments 35 to 37, further comprising a medical monitor comprising a monitor first sensor input port.
39. The system of embodiment 38, wherein the first sensor output port is configured to electrically couple to the monitor first sensor input port of the medical monitor.
40. The system of embodiment 39, further comprising a cable comprising a connector configured to releasably couple to the first sensor output port and the monitor first sensor input port.
41. The system of embodiment 38, wherein the apparatus receives a signal indicative of the first physiological indicator and transmits a replica of the signal indicative of the first physiological indicator to the medical monitor.
42. The system of any of embodiments 38 to 41, wherein the medical monitor comprises a monitor second sensor input port, wherein the second sensor output port is configured to electrically couple to the monitor second sensor input port.

43. The system of any of embodiments 35 to 42, further comprising a patient.
44. The system of any of embodiments 37 to 43, wherein a portion of the core body temperature monitor is releasably attached to the patient.
45. The system of any of embodiments 35 to 44, wherein the core body temperature monitor outputs the core body temperature of the patient as a resistance value.
46. The system of any of embodiments 38 to 45, wherein the medical monitor is communicatively coupled to an electronic health record of the patient and provides a patient identity to the electronic health record, wherein the patient identity is also provided to the apparatus.
47. The system of any of embodiments 37 to 44, wherein the core body temperature monitor is configured to save a plurality of temperature records for the patient into memory.
48. The system of embodiment 47, wherein the apparatus is configured to receive at least some of the plurality of temperature records from the core body temperature monitor.
49. The system of any of embodiments 47 to 48, wherein the apparatus is configured to provide at least some of the plurality of temperature records to the medical monitor.
50. The system of any of embodiments 47 to 49, wherein the apparatus is configured to provide at least some of the plurality of temperature records to the medical monitor prior to transmitting the first temperature though the output port.
51. The system of any of embodiments 47 to 50, further comprising a remote server.
52. The system of embodiment 51, wherein the apparatus is configured to provide at least some of a plurality of records to the remote server.
53. The system of any of embodiments 51 to 52, wherein the plurality of records is matched with the patient identification.
54. The system of any of embodiments 51 to 53, wherein the first or second sensor is communicatively coupled to a logging unit.
55. The system of any of embodiments 51 to 54, wherein the logging unit is communicatively coupled to the remote server.
56. The system of any of embodiments 54 to 55, wherein the logging unit comprises one or more processors communicatively coupled to a memory and a communication module, the memory comprising instructions that when executed by the one or more computer processors cause the one or more computer processors to:
receive the plurality of records from the first sensor,
determine a first location of the first sensor based on a logging unit location;
update a record from the plurality of records with the first location;
transmit an updated record to the remote computer.
57. The system of embodiment 56, wherein the logging unit comprises memory comprising instructions that when executed by the one or more computer processors cause the one or more computer processors to update the temperature record with an ID of the specific logging unit and a time stamp.
58. The system of embodiment 56, wherein the logging unit comprises memory comprising instructions that when executed by the one or more computer processors cause the one or more computer processors to record one or more settings of the apparatus and perform at least one operation in response to the recording.
59. The system of any of embodiments 51 to 58, wherein the remote computer comprises one or more computer processors communicatively coupled to a memory, the memory comprising instructions that when executed by the one or more computer processors cause the one or more computer processors to:
receive a first set of records of the patient indicative of the first sensor at a first location;
receive a second set of records of the patient indicative of the first sensor at a second location; and
perform at least one operation in response to receiving the first set of records and the second set of records.
60. The system of embodiment 58, wherein the remote computer comprises memory comprising instructions that when executed by the one or more computer processors cause the one or more computer processors to perform at least one operation by determining whether hypothermia has occurred in the patient based on the first or second set of records.
61. The system of embodiment 58 or 59, wherein the remote computer comprises memory comprising instructions that when executed by the one or more computer processors cause the one or more computer processors to perform at least one operation by displaying the first set of records and the second set of records as part of the same instance.
61a. The system of any of embodiments 52 to 61, wherein the records are temperature records.
61b. The system of any of embodiments 52 to 61, wherein the records are non-temperature data selected from location data, or sensor ID.
62. The system of any of embodiments 58 to 60, wherein the remote computer comprises memory comprising instructions that when executed by the one or more computer processors cause the one or more computer processors to compare hypothermia rates of the first location and the second location based on different sets of patients.
63. The system of any of embodiments 51 to 62, wherein the remote computer comprises memory comprising instructions that when executed by the one or more computer processors cause the one or more computer processors to:
receive performance data of the apparatus at least partially indicative of a heating cycle.
63a. The system of embodiment 63, further comprising:
determine a duration of the heating cycle based on the performance data;
determine whether the duration meets a duration threshold; and
perform at least one operation responsive to the duration threshold being met.
64. The system of embodiment 63a, wherein to perform at least one operation includes discarding data from the apparatus in response to the duration threshold not being met.
65. The system of embodiment 63a or 64, wherein to perform at least one operation includes:
receiving, from the apparatus, a set of physiological indicators values of the patient associated with the duration;
receiving a medical record of the patient, the medical record including the set of physiological indicators values;

associating the medical record of the patient with the performance data of the apparatus based on a correlation between the set of physiological indicator values received from the apparatus and the set of physiological indicator values received from the medical record.

65a. The system of embodiment 63a or 64 or 65, wherein the performance data of the apparatus includes the duration.

66. The system of any of embodiments 62 to 65, wherein to perform at least one operation includes:
determining an aggregate heating cycle duration across a plurality of heating cycles for the apparatus;
determining whether an aggregate heating cycle duration threshold is met by the aggregate heating cycle duration; and
communicate a maintenance procedure indication based on the aggregate heating cycle duration threshold being met.

We claim:

1. A system for providing pressurized, thermally conditioned air, the system comprising:
an apparatus, comprising;
a casing;
a housing in the casing describing an airflow pathway with an air diffusing outlet proximate to an outlet opening for providing a stream of pressurized air through the outlet opening;
a convective module disposed in a portion of the housing and the outlet opening via the airflow pathway;
a first sensor input port adjacent to a portion of the casing and configured to receive a signal indicative of a first physiological indicator;
a first sensor output port adjacent to a portion of the casing and configured to transmit the signal indicative of the first physiological indicator;
a controller communicatively coupled to the first sensor input port, the first sensor output port, and the convective module, the controller comprising:
an authentication circuit;
one or more computer processors; and
a memory comprising instructions that when executed by the one or more computer processors cause the one or more computer processors to:
evaluate a compatibility of the first sensor output port and the first sensor input port via the authentication circuit;
evaluate a transmission rate of the first physiological indicator to the first sensor input port during a time period associated with at least the first physiological indicator;
transmit the first physiological indicator via the first sensor output port;
determine a first physiological indicator value from the first sensor input port; and
perform at least one operation in response to the determination of the first physiological indicator value; and
a core body temperature sensor coupled with the apparatus, wherein the first physiological indicator comprises a core body temperature.

2. The system of claim 1, wherein to perform at least one operation comprises controlling a portion of the convective module based on the first physiological indicator.

3. The system of claim 1, wherein the controller and the first sensor output port are wired in parallel from the first sensor input port.

4. The system of claim 3, wherein the memory further comprises instructions that when executed by the one or more computer processors cause the one or more computer processors to transmit the first physiological indicator nearly simultaneously as a replica of the signal indicative of the first physiological indicator.

5. The system of claim 1, wherein the first sensor input port comprises a first pin and the first sensor output port comprises a second pin electrically coupled to the first pin.

6. The system of claim 1, further comprising a second sensor input port and a second sensor output port.

7. The system of claim 6, wherein the second sensor input port receives a digital signal indicative of a second physiological indicator, and the first sensor input port receives an analog signal indicative of the first physiological indicator.

8. The apparatus system of claim 7, wherein the first or second physiological indicator is selected from the group consisting skin temperature, pulse oximetry, electrical activity of a heart, and combinations thereof.

9. The system of claim 1, wherein the controller comprises:
the authentication circuit configured to:
receive an identification signal from the first sensor input port or a second sensor input port unique to the first sensor or a second sensor;
determine a sensor type from the identification signal; and
in response to determining that the sensor type is not compatible with the apparatus, transmitting the signal from the first sensor or the second sensor without using the signal to control a convective module.

10. The system of claim 1, wherein the first sensor input port comprises at least one pin that provides power output to the core body temperature sensor.

11. The system of claim 1, further comprising:
a medical monitor, comprising a monitor first sensor input port, wherein the first sensor output port is configured to electrically couple to the monitor first sensor input port of the medical monitor.

12. The system of claim 11, further comprising a cable comprising a connector configured to releasably couple to the first sensor output port and the monitor first sensor input port.

13. The system of claim 11, wherein the apparatus receives a signal indicative of the first physiological indicator and transmits a replica of the signal indicative of the first physiological indicator to the medical monitor.

14. The system of claim 11, further comprising a second sensor having a second sensor output port, wherein the medical monitor comprises a monitor second sensor input port, wherein the second sensor output port is configured to electrically couple to the monitor second sensor input port.

15. The system of claim 11, further comprising a remote computer, wherein the remote computer is configured to receive at least some records corresponding to the first physiological indicator.

16. The system of claim 15, wherein the remote computer comprises one or more computer processors communicatively coupled to a memory, the memory comprising instructions that when executed by the one or more computer processors cause the one or more computer processors to:
receive a first set of records of the patient indicative of the core body temperature sensor at a first location;
receive a second set of records of the patient indicative of the core body temperature sensor at a second location; and
perform at least one operation in response to receiving the first set of records and the second set of records.

17. The system of claim 15, wherein the remote computer comprises memory comprising instructions that when executed by the one or more computer processors cause the one or more computer processors to:
- receive performance data of the apparatus at least partially indicative of a heating cycle;
- receiving, from the apparatus, a set of physiological indicators values of the patient associated with the performance data;
- receiving a medical record of the patient, the medical record including the set of physiological indicators values;
- associating the medical record of the patient with the performance data of the apparatus based on a correlation between the set of physiological indicator values received from the apparatus and the set of physiological indicator values received from the medical record.

18. The system of claim 11, further comprising a logging unit communicatively coupled to the core body temperature sensor and a remote server, wherein the logging unit comprises one or more processors communicatively coupled to a memory and a communication module, the memory comprising instructions that when executed by the one or more computer processors cause the one or more computer processors to:
- receive a plurality of records from the core body temperature sensor;
- determine a first location of the core body temperature sensor based on a logging unit location;
- update a record from the plurality of records with the first location; and
- transmit an updated record to a remote computer.

19. The system of claim 18, wherein the remote computer comprises memory comprising instructions that when executed by the one or more computer processors cause the one or more computer processors to perform at least one operation by displaying a first set of records from the first location and a second set of records from a second location as part of a same instance.

* * * * *